United States Patent [19]

Tsunemi et al.

[11] Patent Number: 4,880,736
[45] Date of Patent: Nov. 14, 1989

[54] PRODUCTION OF URIDINE

[75] Inventors: Yutaka Tsunemi; Satoru Asahi, both of Suita; Muneharu Doi, Takarazuka, all of Japan

[73] Assignee: Takeda Chemical Industries, Ltd., Osaka, Japan

[21] Appl. No.: 788,812

[22] Filed: Oct. 18, 1985

[30] Foreign Application Priority Data

Oct. 26, 1984 [JP] Japan ................................. 59-226515

[51] Int. Cl.$^4$ .......................... C12P 19/38; C12R 1/07
[52] U.S. Cl. ....................................... 435/87; 435/832; 435/836; 435/839
[58] Field of Search ................. 435/87, 253, 832, 839, 435/836, 252.5

[56] References Cited

U.S. PATENT DOCUMENTS 3,139,385  6/1964  Ogata et al. ........................... 195/28

FOREIGN PATENT DOCUMENTS 52-139786  11/1977  Japan .

OTHER PUBLICATIONS

Sakai, T., Tochikura T., and K. Ogata, 1966, Metabolisms of Nucleosides in Bacteria, Apr. Biol. Chem. 30(3), 245–253.

Imada A., and S. Igarasi 1967, Ribosyl and Deoxypribosyl Transfer by Bacterial Enzyme Systems, J. Bacteriol 94(5), 1551–1559.

Jensen K. F., Neuhard J. and L. Schack 1982, RNA Polymerase Involvement in the Regulation of Expression of Salmonella Typhimerrium pyr Genes, Isolation and Characterization of a Fluorouracil—Resistive Mutant with High Constitutive Expression of the pyr B and pyr E Genes Due to a Mutation in rpo BC, EMBO Journal 1(1), 69–74.

Saunders, P. P., Wilson B. A., and G. F. Saunders, 1969, Purification and Comparative Properties of a Pyrimidine Nucleoside Phosphroylose from Bacillus Stearothermophilus. J Bio. Chem. 244: 3691–3697.

O'Donovan G. A., and J. C. Gerhart 1972, Isolation and Partial Characterization of Regulatory, Mutants of the Pyrimidine Pathway in Salmonella Typhimurium, J. Bacteriol 109(3), 1085–1096.

Central Patents Index, Abstracts Journal, Section D, No. 02966A/02, the Abstract of Japanese Patent Publication (laid open) No. 52—139786.

Central Patents Index, Abstracts Journal, Section D, No. 35985A/20, the Abstract of Japanese Patent Publication (laid open) No. 53—38691.

*Primary Examiner*—Charles F. Warren
*Assistant Examiner*—Irene Marx
*Attorney, Agent, or Firm*—Wenderoth, Lind & Ponack

[57] ABSTRACT

Uridine is produced by cultivating in a culture medium a uridine-producing microorganism, which belongs to the genus Bacillus and which is deficient in uridine nucleoside phosphorylase activity and is resistant to a pyrimidine analogue, and recovering the accumulated uridine. This method has the advantage of substantially avoiding the by-production of uracil and uridylic acid.

8 Claims, No Drawings

PRODUCTION OF URIDINE

This invention relates to a fermentative method of producing uridine which is useful as a biochemical reagent (refer to e.g. Methods in Enzymology, Vol. VI, Academic Press, New York and London, 1963, p. 194) or a starting material for synthesizing pharmaceuticals (refer to e.g. Collection Czechosiov. Chem. Commun. Vol. 39, 3100–3108, 1974; Bulletin of the Chemical Society of Japan, Vol. 48(7), 2084–2090, 1975; Chem. Pharm. Bull., Vol. 19, 2466–2471, 1971).

So far, known methods of fermentatively producing uridine use a pyrimidine analogue resistant strain derived from a bacterial strain of the genus Micromonospora [Japanese Patent Publication (laid open) No. 139786/1977 (Tokukaisho No. 52-139786)] and a purine analogue-resistant strain derived from a bacterial strain of the genus Brevibacterium [Japanese Patent Publication (laid open) No. 38691/1983 Tokukaisho No. 53-38691)]. In these methods, uracil and uridylic acid are simultaneously accumulated in the medium.

This invention provides a method of producing uridine in high yields and in an industrially advantageous manner using microorganisms of the genus Bacillus, unlike the methods using microorganisms belonging to the genus Micromonospora or Brevibacterium such as mentioned above.

The present inventors studied intensively in search of a fermentative method of producing uridine using a strain of the genus Bacillus. As a result, they found that a microorganism which belongs to the genus Bacillus and which is deficient in uridine nucleoside phosphorylase activity and is resistant to a pyrimidine analogue can produce and accumulate a significant amount of uridine in the medium. Continued studies based on this finding have now led to completion of the present invention.

Thus, the invention provides a method of producing uridine which comprises cultivating in a medium a uridine-producing microorganism, which belongs to the genus Bacillus and which is deficient in uridine nucleoside phosphorylase activity and is resistant to a pyrimidine analogue, to thereby cause formation and accumulation of uridine in the culture broth, and recovering the accumulated uridine.

The microorganism which "is deficient in uridine nucleoside phosphorylase activity" as used herein means a microorganism having a uridine nucleoside phosphorylase activity value of not more than 0.01 unit (nanomole/min)/mg protein as measured by the method of J. J. Scocca ("Methods in Enzymology", vol. LI, edited by P. A. Hoffee and M. E. Jones, Academic Press, New York, 1978, p. 432, the disclosure of which is incorporated herein by reference). The microorganism which "is resistant to a pyrimidine analogue" means a microorganism derived from a strain belonging to the genus Bacillus as the parent strain and modified in genetic properties such that it can grow in media containing a pyrimidine analogue in high concentrations, e.g. not less than two times, preferably not less than three times, as high as the concentration of the media in which the parent strain cannot grow. The term "pyrimidine analogue" means a substance similar in structure to pyrimidine bases such as uracil and cytosine, for example 6-azauracil, 2-thiouracil, 5-hydroxyuracil, 5-fluorouracil, ribosides of these or ribotides of these. It is sufficient that the pyrimidine analogue-resistant microorganism has resistance to at least one pyrimidine analogue.

Representative examples of the microorganism to be used in the practice of the invention are Bacillus subtilis ST-58 (IFO 14387, FERM BP-855), Bacillus subtilis STA-17 (IFO 14388, FERM BP-856), Bacillus subtilis SA-85 (IFO 14389, FERM BP-860), Bacillus licheniformis LA-2 (IFO 14391, FERM BP-857) and Bacillus pumilus PT-42 (IFO 14390, FERM BP-858).

Of these microorganisms, the strains ST-58 and STA-17 have been derived from Bacillus subtilis No. 122 (IFO 14386, FERM BP-859) as the parent strain; the strain SA-85 from Bacillus subtilis (IFO 13719, ATCC 6051) as the parent strain; the strain LA-2 from Bacillus licheniformis (IFO 12199, ATCC 10716) as the parent strain; and the strain PT-42 from Bacillus pumilus (IFO 12088, ATCC 6632) as the parent strain. Similar uridine-producing microorganisms can be easily derived from other bacterial strains of the genus Bacillus as the parent strain by, for example, known mutation procedures such as ultraviolet irradiation [refer to e.g. J. gen. Microbiol. (1963), 33, p. 367, the disclosure of which is incorporated herein by reference] or treatment with N-methyl-N'-nitro-N-nitrosoguanidine (hereinafter referred to as NTG; refer to e.g. Biochemical and Biophysical Research Communications, Vol. 18, No. 5–6, pp. 788–795, 1965, the disclosure of which is incorporated herein by reference), followed by the selection by the replica method (refer to e.g. Journal of Bacteriology, Vol. 63, pp. 399–406, 1952, the disclosure of which is incorporated herein by reference), for instance, to obtain the mutants having the above-mentioned properties. Thus, it is possible to take any known strain of Bacillus, subject the strain to one of the above mutation procedures to obtain a mutant strain, and then test the mutant strain to determine whether it satisfies the above-requirements of the present invention concerning uridine nucleoside phosphorylase activity and resistance to a pyrimidine analogue, and is therefore suitable for use in the invention.

Of the parent strains mentioned above, Bacillus subtilis (IFO 13719, ATCC 6051), Bacillus licheniformis (IFO 12199, ATCC 10716) and Bacillus pumilus (IFO 12088, ATCC 6632) are known strains each listed in List of Cultures, Sixth Edition, 1978 published by Institute for Fermentation, Osaka (IFO), Japan, and in Catalogue of Strains I, Fifteenth Edition, 1982, published by American Type Culture Collection (ATCC), U.S.A. The strain Bacillus subtilis No. 122 (IFO 14386, FERM BP-859) is a strain newly isolated from soil by the present inventors and has the following bacteriological properties:

A. Morphology (1) Shape and size: Short rods (0.7 to 0.8 $\times$ 2.5 to 3.0$\mu$)
(2) Polymorphism: Single, occasionally double
(3) Motility: —
(4) Sporulation: +
(5) Shape of spores: Oval
(6) Position of spores: In the vicinity of the center
(7) Gram staining: Positive
(8) Acid resistance: —

B. State of growth (1) Bouillon agar plate culture: Indeterminate in form and diffusive; rough and flat surface; opaque and light brown (2) Bouillon liquid culture: Pellicle formation on the surface; no turbidity
(3) Litmus milk: Peptonization; reduction of pigments C. Physiological properties (1) Reduction of nitrates: +
(2) V-P test: Positive
(3) Hydrolysis of starch: +
(4) Utilization of citric acid: +
(5) Utilization of propionic acid: −
(6) Utilization of ammonium salts: +
(7) Urease: Weak
(8) Catalase: +
(9) Behavior to oxygen: Aerobic
(10) Resistance to sodium chloride: Able to grow at 7%
(11) Acid resistance: Able to grow at pH 5.7.

Referring to Bergy's Manual of Determinative Bacteriology, Eigth Edition, edited by R. E. Buchanan and N. E. Gibbons, 1974, this strain having the above bacteriological properties has been identified as a microorganism belonging to the species *Bacillus subtilis*.

The IFO numbers disclosed herein are the deposit numbers for the respective microorganisms deposited with the Institute for Fermentation, Osaka (IFO; 17-85 Jusohonmachi 2-chome, Yodogawa-ku, Osaka, Osaka Prefecture, Japan) and the Ferm P- numbers are those for the microorganisms deposited with the Fermentation Research Insitute, Agency of Industrial Science and Technology, Ministry of International Trade and Industry, Japan (FRI; 1-3 Yatabecho Higashi 1-chome Tsukuba-gun, Ibaraki Prefecture, Japan). The deposits at FRI were made under the following accession numbers, on Oct. 19, 1984, and converted to deposits under the Budapest Treaty with the indicated deposit numbers.

| Original Accession No. | Deposit No. under the Budapest Treaty |
| --- | --- |
| FERM P-7904 | FERM BP-855 |
| FERM P-7905 | FERM BP-856 |
| FERM P-7906 | FERM BP-857 |
| FERM p-7907 | FERM BP-858 |
| FERM P-7908 | FERM BP-859 |
| FERM P-7909 | FERM BP-860 |

The Bacillus strains to be used in producing uridine in accordance with the invention have the same bacteriological properties as the respective parent strains except for the deficiency in uridine nucleoside phosphorylase activity, the resistance to a pyrimidine analogue and the ability to produce uridine.

The uridine-producing microooorganisms obtained in the above manner are cultivated in the same manner as the conventional cultivation of microorganisms. Thus, as the medium, there may be used a liquid culture medium containing a carbon source or sources, a nitrogen source or sources and metal ions and, as necessary, other nutrients such as amino acids, nucleic acids and vitamins. As the carbon source, for instance,, there may be used glucose, sucrose, maltose, starch, saccharified starch, molasses and so forth. As the nitrogen source, there may be used organic nitrogen sources such as peptone, corn steep liquor, soybean meal, yeast extract and urea, and, further, inorganic nitrogen sources such as ammonium salts of sulfuric, nitric, hydrochloric, carbonic and other acids, gaseous ammonia and aqueous ammonia, either singly or in combination. As other nutrients, inorganic salts, amino acids, vitamins and so forth necessary for the bacterial growth are appropriately selected and used either singly or in combination. Furthermore, an antifoaming agent or surfactant such as silicone oil or polyalkylene glycol ether may be added to the medium as necessary. The cultivation is generally carried out under aerobic conditions such as those of shake culture or submerged culture with aeration and stirring. The medium preferably has a pH within the range of 4 to 9. When pH variation is observed during cultivation, sulfuric acid, calcium carbonate, sodium hydroxide, gaseous ammonia or aqueous ammonia, for instance, may appropriately be added to adjust the pH to a value falling within the preferred range mentioned above. The cultivation temperature is generally selected within the range of 20° C. to 45° C. so that it may be appropriate for the growth of the microorganism used and for the accumulation of uridine. The cultivation is preferably conducted until the accumulation of uridine becomes substantially maximal. Generally, 2 to 6 days of cultivation achieves this end.

For the separation and recovery of uridine from the resultant culture broth, there may be used per se known usual techniques of purification, for example such separation and purification techniques as precipitation and chromatography using an ion exchange resin or activated carbon.

The method of producing uridine according to the present invention is very advantageous from the industrial point of view in that it causes accumulation of uridine in larger amounts, the uridine accumulation in the culture medium is selective with little or no coproduction of uracil or uridylic acid, and accordingly separation and purification of uridine are relatively easy.

In the Examples shown in the following, the present invention is described still more concretely; however, this does not mean that the scope of the present invention is limited to them.

EXAMPLE 1

A medium prepared by supplementing a basal medium (A) having the composition given below with 100 μg/ml of uracil was streaked with *Bacillus subtilis* No. 122 (IFO 14386, FERM BP-859) which had been treated with 50 μg/ml of NTG for 20 minutes (hereinafter, the NTG treatment was conducted under the same conditions as just mentioned), followed by incubation at 37° C. for 3 days. From among the colonies that had appeared, a uracil-requiring mutant strain was selected by the replica plating method. This uracil-requiring strain was subjected to NTG treatment. The basal medium (A) supplemented with 100 μg/ml of uracil was streaked with said strain and incubation was performed at 37° C. for 3 days.

| Basal medium (A) | | | |
| --- | --- | --- | --- |
| Glucose | 2.0% | Ammonium sulfate | 0.5% |
| Sodium glutamate | 1.0% | Magnesium sulfate | 0.01% |
| Dipotassium phosphate | 0.1% | Biotin | 0.1 mg/liter |
| Agar | 2.0% | (pH 7.0) | |

The colonies which had appeared were transferred, by replica plating, onto a medium composed of the basal medium (A) and 100 μg/ml of uridine added thereto. In this way, a strain incapable of growing on the medium (uridine nucleoside phosphorylase activity-deficient strain) was selected. The thus-obtained, uridine nucleoside phosphorylase activity-deficient strain was streaked onto the basal medium (A), and a strain which had resumed the property of requiring uracil as a result of spontaneous mutation was selected. This revertant strain was then subjected to NTG treatment and streaked onto a medium (A-T) prepared by adding 100 μg/ml of 2-thiouracil to the basal medium (A). Incubation was conducted at 37° C. for 4 days. From among the colonies appearing on the medium (A-T), a uridine-producing strain, *Bacillus subtilis* ST-58 (IFO 14387, FERM BP-855), was selected. Then, this *Bacillus subtilis* ST-58 was treated with NTG and streaked onto a medium (A-A) prepared by adding 200 μg/ml of 6-azauracil to the basal medium (A), followed by incubation at 37° C. for 4 days. From among the colonies that had appeared, a strain high in ability to produce uridine, *Bacillus subtilis* STA-17 (IFO 14388, FERM BP-856), was selected. The uridine nucleoside phosphorylase activity (determined by the method of J. J. Scocca (vide supra)) and extents of resistance to various pyrimidine analogues of each of the above-mentioned strains were as shown in Table 1 and Table 2, respectively.

TABLE 1

| Bacterial strain | Uridine nucleoside phosphorylase activity (*1) |
| --- | --- |
| *Bacillus subtilis* ST-58 | 0.002 |
| *Bacillus subtilis* STA-17 | 0.002 |
| *Bacillus subtilis* No. 122 | 0.045 |

(*1) Unit/mg of protein

TABLE 2

| Additive to basal medium (A) | Growth of strain* | | |
| --- | --- | --- | --- |
| | No. 122 | ST-58 | STA-17 |
| No additive | + | + | + |
| 6-Azauracil, 100 μg/ml | − | + | + |
| 200 | − | − | + |
| 2-Thiouracil, 100 | − | + | + |
| 200 | − | − | + |
| 5-Fluorouracil, 50 | − | + | + |
| 5-Hydroxyuracil, 10,000 | − | + | + |
| 5-Fluoroorotic acid, 100 | − | + | + |

*+: Growth, −: No growth

A 20-ml fermentation medium comprising 15% glucose, 3% corn steep liquor, 1% urea and 2% calcium carbonate placed in a 200-ml flask was inoculated with each of the above microorganisms and shake culture was performed at 37° C. for 3 days to give the results shown in Table 3.

TABLE 3

| Bacterial strain | Uridine accumulation |
| --- | --- |
| *Bacillus subtilis* ST-58 | 12 mg/ml |
| *Bacillus subtilis* STA-17 | 20 mg/ml |
| *Bacillus subtilis* No. 122 | 0 mg/ml |

EXAMPLE 2

Following the procedure of Example 1, a uridine nucleoside phosphorylase activity-deficient strain was obtained from *Bacillus subtilis* (IFO 13719, ATCC 6051). After NTG treatment of this uridine nucleoside phosphorylase activity-deficient strain, a strain, *Bacillus subtilis* SA-85 (IFO 14389, FERM BP-860) was selected as a strain capable of growing on a medium prepared by adding to the basal medium (A) 6-azauracil in a concentration (100 μg/ml) in which the parent strain could not grow. The uridine nucleoside phosphorylase activity of this strain was measured to be 0.003 unit/mg of protein (that of the parent strain being 0.033 unit/mg of protein). *Bacillus subtilis* SA-85 was then cultivated under the same conditions as used in Example 1, whereupon the uridine accumulation amounted to 5.2 mg/ml.

EXAMPLE 3

*Bacillus licheniformis* (IFO 12199, ATCC 10716) was subjected to NTG treatment in the same manner as Example 1, followed by streaking therewith a medium prepared by adding 50 μg/ml of 5-fluorouridine to the basal medium (A) shown in Example 1. Incubation was performed at 37° C. for 4 days and the resultant colonies were tested for uridine nucleoside phosphorylase activity. About half of the colonies were found to be deficient in said enzyme. One of the thus-obtained uridine nucleoside phosphorylase activity-deficient strains was irradiated with ultraviolet rays by a conventional method. A medium prepared by adding, to the basal medium (A), 6-azauracil in a concentration (100 μg/ml) in which the parent strain could not grow was streaked with the ultraviolet-irradiated strain, followed by incubation at 37° C. for 4 days. From among the colonies that had appeared, a uridine-producing strain, *Bacillus licheniformis* LA-2 (IFO 14391, FERM BP-857), was selected. The parent strain and the mutant (LA-2) were compared with respect to uridine nucleoside phosphorylase activity. The parent strain showed an activity of 0.030 unit/mg of protein, whereas the activity with the mutant was 0.009 unit/mg of protein. Cultivation of the thus-obtained strain *Bacillus licheniformis* LA-2 under the same conditions as used in Example 1 resulted in accumulation of 3 mg/ml of uridine. On the other hand, no uridine accumulation was observed in the cultivation of the parent *Bacillus licheniformis* strain (IFO 12199, ATCC 10716) under the same conditions as mentioned above.

EXAMPLE 4

A uridine nucleoside phosphorylase activity-deficient strain was obtained from *Bacillus pumilus* (IFO 12088, ATCC 6632) in the same manner as Example 1. Then, this uridine nucleoside phosphorylase activity-deficient strain was treated, with NTG, and a strain, *Bacillus pumilus* PT-42 (IFO 14390, FERM BP-858), was selected as a strain capable of growing in a medium prepared by adding, to the basal medium (A) shown in Example 1, 2-thiouracil in a concentration (600 μg/ml) in which the parent strain could not grow. The uridine nucleoside phosphorylase activity with this strain was found to be 0.007 unit/mg of protein (that for the parent strain being 0.057 unit/mg of protein). Cultivation of *Bacillus pumilus* PT-42 under the same conditions as used in Example 1 resulted in accumulation of 5 mg/ml of uridine.

EXAMPLE 5

Using fifty 200-ml flasks each containing 20 ml of the fermentation medium specified in Example 1, *Bacillus subtilis* STA-17 was cultivated in accordance with Example 1. The culture broth obtained was deprived of cells by centrifugation, the supernatant was adjusted to pH 2.0 with 1N hydrochloric acid, and the resultant precipitate was removed by centrifugation. The supernatant thus obtained was applied to an activated carbon column for adsorption of uridine, followed by elution with 50% ethanol containing 1.4% aqueous ammonia. Uridine-containing eluate fractions were combined and concentrated under reduced pressure, and the concentrate was adjusted to pH 8.0 with aqueous ammonia, followed by addition of an equal volume of 0.01M potassium borate. The resultant mixture was applied to a Dowex-1×2 (Cl⁻ form, 200–400 mesh) column for adsorption of uridine. This column was washed with distilled water and then elution of uridine was performed using an aqueous solution containing 0.03M potassium chloride and 0.02M potassium borate per liter. Uridine-containing eluate fractions were combined and the borate was removed by repeated addition of an equal volume of methanol followed by concentration to dryness. The solid matter thus obtained was dissolved in a small amount of water and, with cooling, alcohol was added to the solution. Crude crystals of uridine were thus obtained (15 g). They were dissolved in a small amount of hot water and the solution was again cooled to give 11 g of uridine as crystals.

What is claimed is:

1. A method of producing uridine, which comprises cultivating in a culture medium a uridine-producing mircroorganism, which is a mutant selected from the group consisting of *Bacillus subtilis* ST-58 (IFO 14387, FERM BP-855), *Bacillus subtilis* STA-17 (IFO 14388, FERM-BP-856), *Bacillus subtilis* SA-85 (IFO 14389, FERM BP-860), *Bacillus licheniformis* LA-2 (IFO 4391, FERM BP-857) and *Bacillus pumilus* PT-42 (IFO 14390, FERM BP-858) which is deficient in uridine nucleoside phosphorylase activity and is resistant to a pyrimidine analogueue, to thereby cause formation and accumulation of uridine in the resultant culture broth, and recovering the uridine from the culture broth.

2. A method according to claim 1, wherein the pyrimidine analogue is 6-azauracil, 2-thiouracil, 5-hydroxyuracil, 5-fluorouracil, a riboside thereof or a ribotide thereof.

3. A method according to claim 1, wherein the pyrimidine analogue is 6-azauracil.

4. A method according to claim 1, wherein the mircroorganism is *Bacillus subtilis* ST-58 (IFO 14387, FERM BP-855).

5. A method according to claim 1, wherein the microorganism is *Bacillus subtilis* STA-17 (IFO 14388, FERM BP-856).

6. A method according to claim 1, wherein the microorganism is *Bacillus subtilis* SA-85 (IFO 14389, FERM BP-860).

7. A method according to claim 1, wherein the microorganism is *Bacillus licheniformis* LA-2 (IFO 14391, FERM BP-857).

8. A method according to claim 1, wherein the microorganism is *Bacillus pumilus* PT-42 (IFO 14390, FERM BP-858).

* * * * *